(12) United States Patent
Baldwin

(10) Patent No.: US 6,405,726 B1
(45) Date of Patent: Jun. 18, 2002

(54) RESUSCITATION DEVICE AND METHOD OF MAKING THE SAME

(76) Inventor: Gene R. Baldwin, 324 Gardiner, Rockford, IL (US) 61107

( * ) Notice: Subject to any disclaimer, the term of this patent is extended or adjusted under 35 U.S.C. 154(b) by 0 days.

(21) Appl. No.: 09/777,456

(22) Filed: Feb. 12, 2001

Related U.S. Application Data

(62) Division of application No. 09/270,899, filed on Mar. 15, 1999, now Pat. No. 6,209,537.

(51) Int. Cl.⁷ ............................................. A61M 16/00
(52) U.S. Cl. ............................ 128/202.28; 128/202.29; 128/202.3
(58) Field of Search ...................... 128/202.28, 202.29, 128/202.3

(56) References Cited

U.S. PATENT DOCUMENTS

| | | | | |
|---|---|---|---|---|
| 4,819,628 A | * | 4/1989 | Eisenberg et al. ...... | 128/202.28 |
| 5,469,842 A | * | 11/1995 | Flynn .................... | 128/202.28 |
| 5,664,559 A | * | 9/1997 | Baldwin ................ | 128/202.28 |
| 5,735,265 A | * | 4/1998 | Flynn .................... | 128/202.28 |

* cited by examiner

Primary Examiner—John G. Weiss
Assistant Examiner—Mital Patel
(74) Attorney, Agent, or Firm—Harold A. Williamson

(57) ABSTRACT

A manually manipulated resuscitation mask, which includes a flexible barrier for providing a sealing contact with a face of a victim in a region adjacent to a victim's mouth. The flexible barrier has an opening therethrough to cooperate with the victim'2 mouth. The opening in the sheet us comprised of an integrally connected, flexible sleeve, extending away from the flexible sheet and the victim's face. The sleeve has an open end remote from where the sleeve is integrally connected to the flexible barrier sheet. The mask also includes a tubular member that has first and second end portions. The tubular member is positionable within the flexible sleeve and has the first end portion integrally secured to the open end of the flexible sleeve. The second end portion of the tubular member is located adjacent to the flexible barrier sheet when the tubular member is positioned within the sleeve. The sleeve and tubular member allow a mouth of a rescuer, when engaging the flexible sleeve and tubular member, to deliver air from the lungs and mouth of a rescuer to and through the tube to the mouth of the victim. A one-way-valve and a filter or combination thereof are fitted into the tubular member.

The tubular member is manually movable such that the second end portion of the tubular member may extend through the flexible sheet to engage a mouth of a victim.

11 Claims, 3 Drawing Sheets

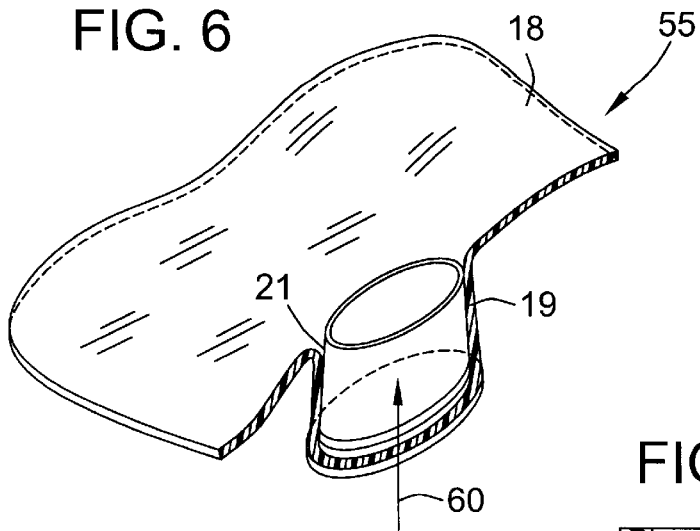
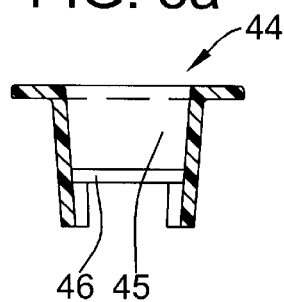
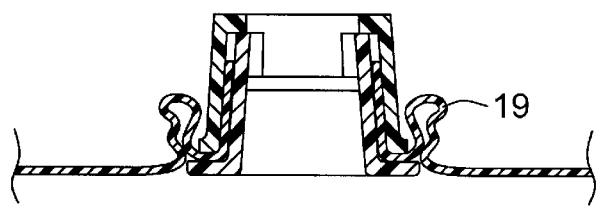
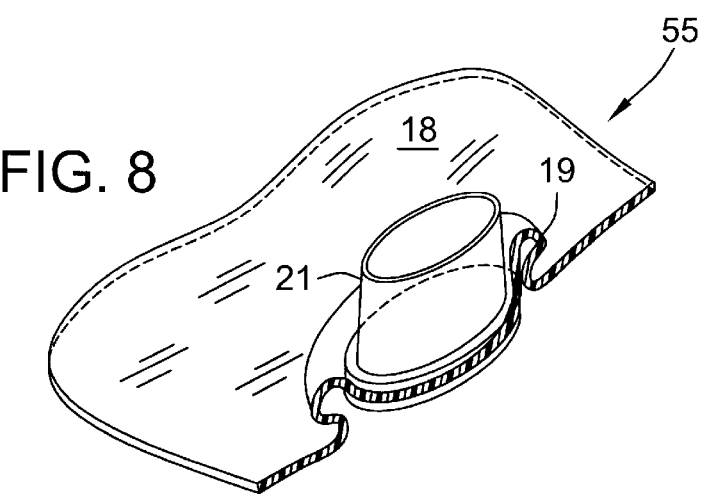
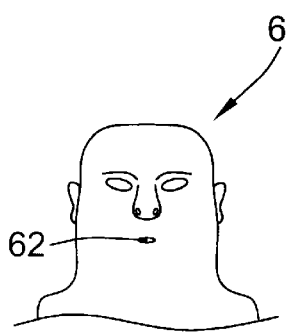
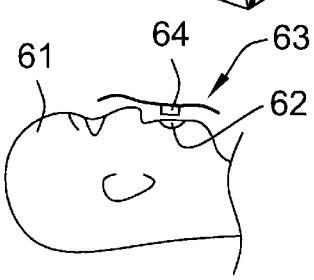
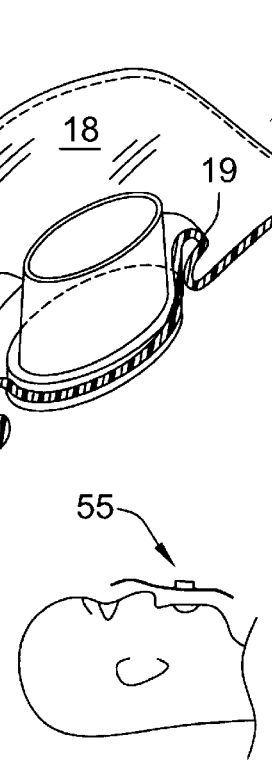

RESUSCITATION DEVICE AND METHOD OF MAKING THE SAME

This application is a division of my co-pending prior U.S. patent application Ser. No. 09/270,899 filed Mar. 15, 1999, now U.S. Pat. No. 6,209,537 the benefit of which filing date is claimed under 35 U.S.C. 120.

FIELD OF INVENTION

Mouth-to-mouth resuscitation devices of the type having a one-way valve through which air is delivered from a resuscitator's mouth to a victim's mouth and lungs through the valve.

BACKGROUND OF THE INVENTION

The effective use of mouth-to-mouth resuscitation devices often depends upon how easy it is for a user of the device to be trained in its use. Classes in cardiopulmonary resuscitation often include ordinary citizens with no paramedical background as well as individuals in training for positions as paramedics. Equipment available for training ranges from those rare settings in which anatomically correct mannequins are provided to practice pulmonary resuscitation, to those settings where a mannequin's head resembles a human head and face only in that there is suggestion of facial feathers. The heads are normally formed of hard, hollow plastic. These suggested features usually include raised portions representative of a nose and forehead. Indentations may appear where eyes would be located and a small circular or oval opening is providing to simulate a mouth. More often than not the mannequin's head size more nearly matches an average adult head rather than a child or infant. Among the most popular resuscitation masks in industrial and commercial settings are those that include a physical shield between a rescuer and a victim requiring mouth-to-mouth resuscitation. The shield frequently takes the form of a flexible sheet having a centrally formed opening and a rigid tube secured to the sheet around the periphery of the opening. The rigid tube is intended to fit within a victim's mouth. The tube routinely includes a one-way valve to allow breath exhaled by the rescuer to pass through the tube/one-way valve and into the mouth and lungs of the victim. The one-way valve and shield act to prevent exhaled or regurgitated matter of the victim from entering the mouth of the rescuer.

Typical of such devices is that shown and described in Eisenberg et al. U.S. Pat. No. 4, 819, 628 ('628) issued Apr. 11, 1989, which shows and describes a device that includes a flexible sheet having an opening centrally formed therein and a rigid tube secured to the sheet around the periphery of the opening for insertion into a mouth of a victim. A self-closing one-way valve is contained in the tube and extends downward from the sheet opening.

A highly enhanced version of a resuscitation mask that also includes a flexible sheet with rigid tube located and secured into the flexible sheet in a similar fashion to the '628 patent is applicant's own double shield mouth-to-mouth resuscitator mask with a barrier for contaminated fingers, namely Baldwin U.S. Pat. No. 5,664,559 ('559) issued Sep. 9, 1997. This patent distinguishes over the '628 patent in that there is provided a second flexible barrier in the form of a thin sheet of flexible material that has an opening the periphery of which is secured to a first flexible barrier and a rigid tube containing a one-way-valve to thereby provide a spatially separated region between the first and second barriers to thereby isolate the mouth and face of the operator from the area where the operator's fingers/hands make contact on the first flexible barrier.

Another resuscitation mask of this type is shown and disclosed in applicant's co-pending patent application Ser. No. 09/128,112, filed Aug. 3, 1998, titled Resuscitation Device with Instantly Closing Valve. A unique aspect of this invention resides in the employment of a flexible sleeve integrally secured to a flexible barrier sheet. At an outlet end of the flexible sleeve, the sleeve has fashioned therein a rigid member to create a one-way valve against the rigid member. The flexible sleeve is stretched to open the one-way valve when air is delivered to an inlet opening of the sleeve and then to and through the sleeve and past a flexible seal of the one-way valve. Positive, instant closing is provided when air is no longer delivered to the inset opening. The invention just described provides a resuscitation device free of a valve housing, thereby allowing the device to be folded into a flat configuration to be readily carried in a billfold, thus encouraging its use by laymen.

In training situations both instructor and trainee are faced with the reality that the rigid tube that is normally inserted into a victim's mouth must now be inserted into the circular or oval mouth opening of the mannequin's head. Rarely is the mannequin mouth opening of a size that adequately accommodates the rigid tube. It is not uncommon for the attempted application of the mask to the mannequin's face to result in the rigid tube secured to the flexible barrier to buckle in the region where the tube joins the barrier. When this happens, the tube opening that is intended to engage the mannequin's mouth opening topples onto its side, making it nearly impossible for the instructor or rescuer in training to place his/her mouth in the opposite side of the barrier and over the other end of the tube.

it is not surprising to find that instructors favor less effective resuscitation masks for certain kinds of mannequin's that do not have any part thereof that enter the mouth when in use.

The subject invention avoids all these problems by recognizing that the rigid tube must be secured to the flexible barrier by a means that allows the rigid tube to remain perpendicular to the flexible barrier and/or mouth region of a mannequin or victim where the victim's mouth can only be partially opened. The mask incorporating the subject invention not only provides a rigid tube covered by a sleeve portion of the flexible barrier that may engage a partially open mouth of a victim, while simultaneously converting to a mask with the rigid tube extending toward the victim's face by the simple application of a force pressing on the tube toward the face of the victim as the mask is about to be placed on a victim's face.

SUMMARY OF THE INVENTION

The invention is directed to a mouth-to-mouth, manually manipulated resuscitation mask, which includes a flexible barrier for providing a sealing contact with a face of a victim in a region adjacent to a mouth of a victim. The flexible barrier is comprised of a thermoplastic sheet having an opening therethrough to cooperate with a mouth of a victim. The opening in the sheet is comprised of an integrally connected, flexible sleeve, extending away from the flexible sheet and the victim's face. The sleeve has an open end remote from where the sleeve is integrally connected to the flexible barrier sheet. The mask also includes a tubular member that has first and second end portions. The tubular member is positionable within the sleeve and has the first end portion integrally secured to the open end of the sleeve.

The second end portion of the tubular member is located adjacent to the flexible barrier sheet when the tubular member is positioned within the sleeve. The sleeve and tubular member as just described are readily available to engage a mouth of a rescuer to deliver air from lungs and mouth of a rescuer to and through the tube to the mouth of a victim. Typically a one-way-valve and a filter or combinations thereof are fitted into the tubular member.

The tubular member is manually moveable such that the second end portion of the tubular member may extend through the flexible sheet to engage a mouth of a victim, while simultaneously allowing their lips to press against the flexible sheet to seal the sheet against the victim's face.

The invention further contemplates the inclusion of a method to produce the manually manipulated resuscitation mask. In a preferred embodiment the method involves differential pressure forming a resuscitation mask of the type that may include a one-way valve and does include a thermoplastic flexible barrier sheet hermetically secured to a tubular member through which air is delivered from a rescuer's mouth to a victim's mouth and lungs.

The method is comprised of the following steps which include placing the tubular member in engagement with a porous plate such that a central axis of the tubular member is essentially perpendicular to the porous plate.

The next step involves locating the thermoplastic, flexible barrier sheet between the tubular member and a source of heat, followed by activating the source of heat to soften the thermoplastic flexible barrier sheet.

This step is succeeded by establishing a low-pressure region on a side of the porous plate opposite to the porous plate side on which the tubular member has engaged the porous plate. The low pressure region thereby causes a differential pressure across the porous plate that results in the softened thermoplastic flexible barrier sheet being drawn towards the tubular member and taking on a new shape, such that at least a portion of the tubular member becomes sandwiched between the softened flexible sheet and the porous plate.

The softened thermoplastic flexible barrier sheet is the cooled to thereby cause the flexible thermoplastic sheet to maintain it's new shape. Thereafter an opening is created through the flexible sheet in a region where the surface of the flexible sheet is defined by the tubular member.

The final step involves inserting into the tubular member, through the opening in the flexible thermoplastic sheet, an insert. The insert mates with the flexible sheet to help secure the flexible sheet to the tubular member. It is therefor a primary object of this invention to provide a resuscitation mask which easily allows a user of the mask to adjust a victim's mouth-engaging portion of the mask such that the mask may engage a face surface of a victim or physically enter an open mouth.

Another object of the invention is to provide an adjustable resuscitation mask that cooperates effectively with a wide variety of the mouth openings found in training mannequins.

Yet another object of this invention is to provide a simple differential pressure forming method for creating an adjustable resuscitation mask.

BRIEF DESCRIPTION OF THE DRAWINGS

The description set forth above, as well as other objects, features and advantages of the present invention, will be more fully appreciated by referring to the detailed description and the drawings that follow. The description is of the presently preferred, but nonetheless illustrative, embodiment in accordance with the present invention, when take in conjunction with the accompanying drawings wherein:

FIG. 5a is a partial section of an insert of FIG. 5 fitted with a one-way valve and a filter;

FIG. 6 is a three dimension graphic of a resuscitation mask embodying the invention with a portion removed to reveal the details of the arrangement;

FIG. 7 is a cross-section of a resuscitation mask embodying the invention where the mask tubular member has been moved to another operating;

FIG. 8 is a three dimensional illustration of the mask arrangement of FIG. 7;

FIG. 9 is a schematic representation of a training mannequin head;

FIG. 10 is a side view of the training mannequin head of FIG. 9 along with a prior art resuscitation mask in place; and FIG. 11 is a side view of the training mask of FIG. 9 with resuscitation mask that embodies the invention in place on the mannequin face.

DETAILED DESCRIPTION OF THE PREFERRED EMBODIMENT

Figure 1:
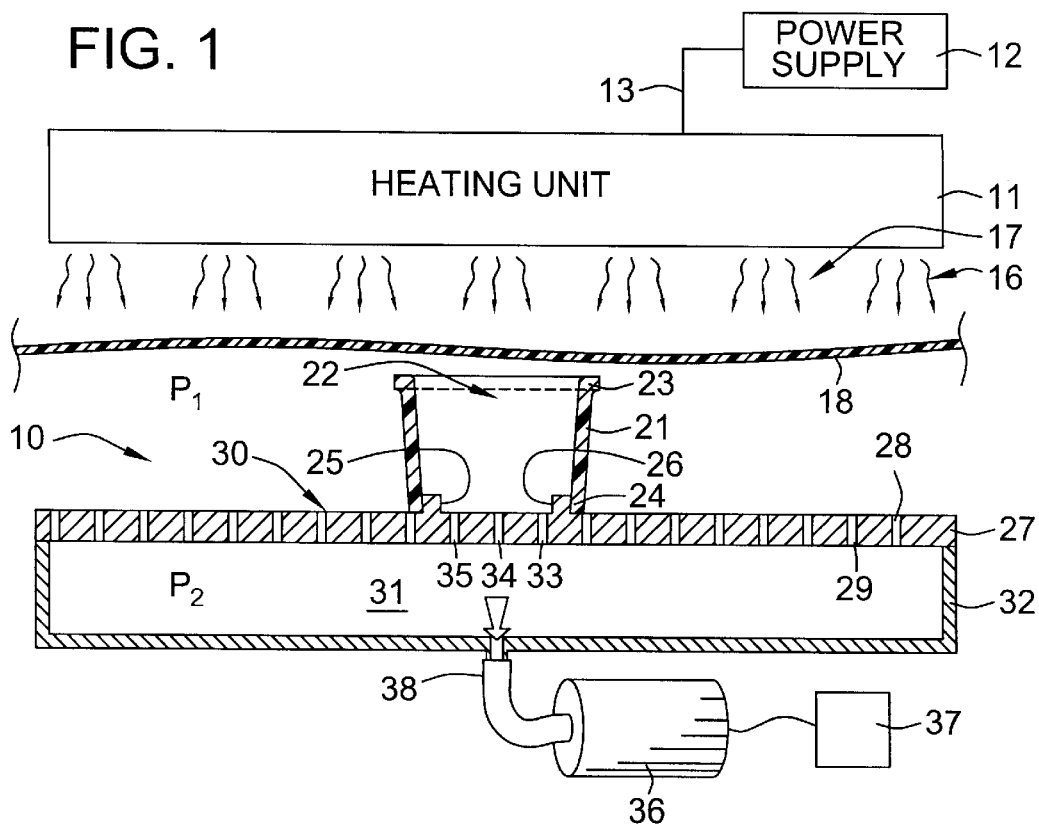
FIG. 1 is a schematic arrangement of components involved in the differential pressure forming of a resuscitation mask that incorporates the invention.
Figure 2:
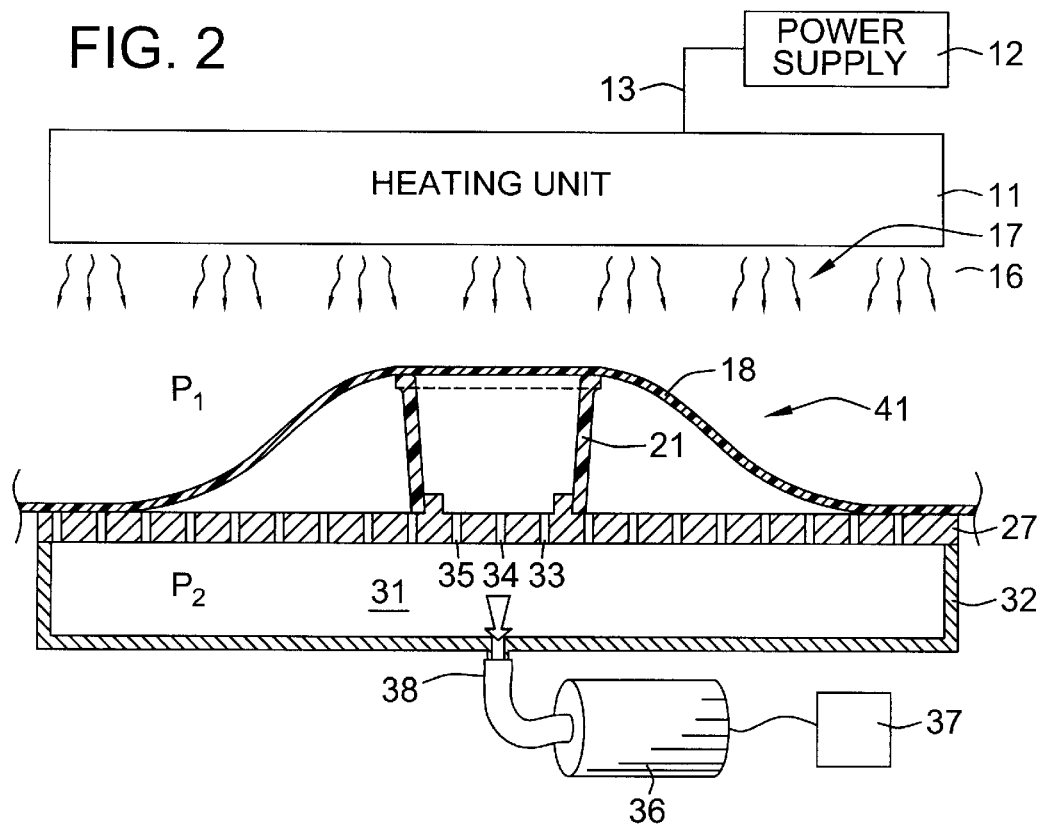
FIG. 2 depicts a flexible thermoplastic barrier sheet in a softened state.
Figure 3:
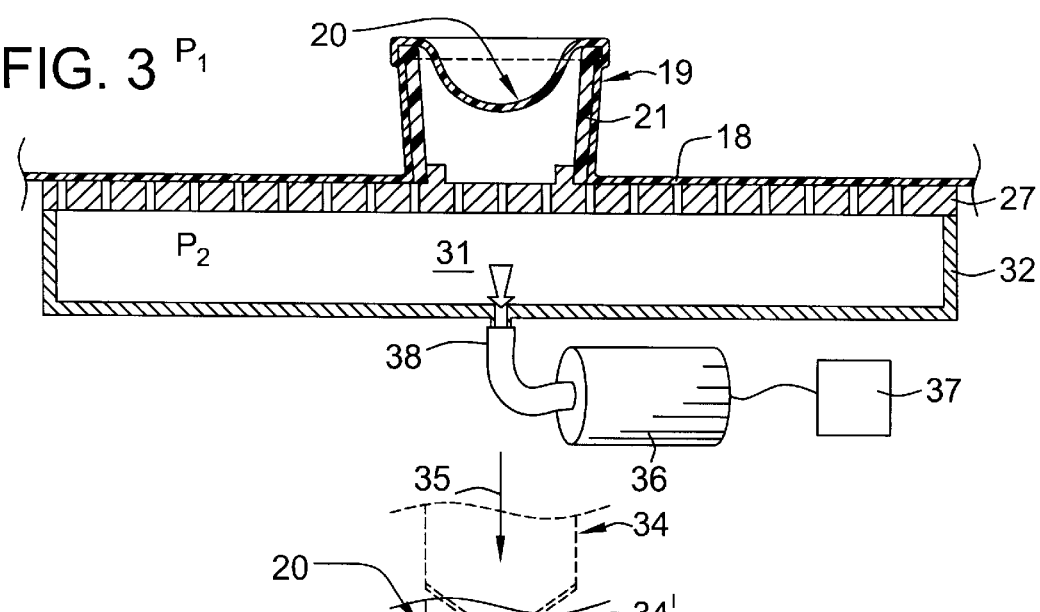
FIG. 3 shows the effect of a differential pressure environment on the arrangement of FIG. 2.

Reference is now made to FIG. 1, which depicts in a schematic illustration the basic components needed to make and practice the subject invention. Centrally disposed in FIG. 1, a thermoplastic flexible barrier sheet 18 is shown midway between a controllable heating unit 11 and a differential pressure creating arrangement 10. This arrangement 10 includes a porous plate 27, which is made porous by apertures such as passages 28, 29, 33, 34, and 35, five of which are referenced. This plate 27 may also be termed a support means. Beneath porous plate 27 is what will be termed a vacuum chamber 31. The vacuum chamber 31 has a vacuum chamber wall 32, which engages the porous plate 27 as shown. A vacuum pump 36 and its related vacuum pump control 37, as referenced in FIGS. 1, 2, and 3, are connected via a vacuum pump duct 38, as shown. It will be noted that centrally disposed on the porous plate surface 30 are a pair of locator pins, 25, 26, shown in cross section. The detailed nature of these locator pins 25, 26, and the manner in which they are secured to or are part of the porous plate 27 do not form a part of the instant invention. These locator pins 25, 26 do act, however, to centrally locate on the porous plate 27 a tubular member 21. It is this tubular member 21 that will ultimately provide an open passage 22 for the flow of air from a rescuer's mouth to that of a victim, all in a manner to be described more fully later. The tubular member 21 has a first end 23, which a later description will reveal engages a rescuer's mouth. The tubular member 21 also has a second end 24, which is shown centered on locator pins 25, 26, on the surface 30 of the porous plate 27. It is this second end 24 of the tubular member 21 that will, in a fully formed resuscitation mask, engage a mouth of a victim to be resuscitated.

At the very top of FIG. 1 there is shown a heating unit 11 and related power supply 12, connected by a lead 13 to the heating unit 11. A series of jagged arrows 16, 17, two of which are referenced and are shown extending downward from the heating unit 11. These jagged arrows are intended to convey visually the notion of radiant heat emanating from the heating unit 11 toward the thermoplastic flexible barrier sheet 18, shown immediately below in FIG. 1. On the left hand side of FIG. 1, in a space between the thermoplastic flexible barrier sheet 18 and the surface 30 of the porous plate 27, a reference character $P_1$ is shown. The character $P_1$ is intended to designate ambient air pressure in which the apparatus of FIG. 1 operates. Visually, directly beneath the ambient pressure character $P_1$ there will be seen a character $P_2$ located in the vacuum chamber 31. This character is intended to represent a pressure lower than ambient pressure $P_1$ brought about by activation of the vacuum pump 36 and it's related control 37. It is the difference in pressure between $P_1$ and $P_2$ that is hereinafter defined as the "differential pressure" employed in the explanation of the method that embodies the invention.

Reference is now made to FIG. 2, which is intended to show what happens to the thermoplastic barrier sheet 18 after the heating unit 11 has been activated for a time sufficient for the thermoplastic of which the barrier sheet is composed, to soften. Note how the softened thermoplastic barrier sheet 18 is shown draped over the porous plate 27 and tubular member 21, all as indicated by reference numeral 41 and associated arrow. In FIG. 2 pressures $P_1$ and $P_2$ are assumed to be equal in that the vacuum pump 36 and related control 27 have not been activated.

Attention is now directed to a study of FIGS. 2 and 3, which should be examined together in conjunction with the explanation that follows. FIG. 3 is intended to convey what happens when the vacuum pumps 36 and control 37 have been turned on, thereby reducing the pressure $P_2$ in the vacuum chamber 31. When pressure $P_2$ falls below the ambient pressure $P_1$ the thermoplastic flexible barrier sheet 18 in its softened and draped state, as shown in FIG. 2, is now drawn down onto the tubular member 21 and the porous plate 27 in the manner depicted. It should also be appreciated that the invention may be practiced by removing the passages 33, 34, 35 from the porous plate 27. When these passages are removed, the thermoplastic flexible sheet will nestle, that is, to settle snugly, into the tubular member 21. The sheet 18 will remain snug, much like that shown in FIG. 2. However, a seal will exist where the flexible sheet 18 engages the tubular member 21. When attention is directed to a preferred embodiment of the invention as shown in FIG. 3, and specifically to the tubular member 21, it will be observed that the softened and now differential pressure drawn thermoplastic barrier sheet 18 has moved toward and then around the tubular member 21, and has taken on a new shape, as shown. The new shape is one, which sandwiches the tubular member 21 between the sheet 18 and the porous plate 27. This new shape may be characterized as one in which there is now present a sleeve 19 that now surrounds the tubular member 21. It is also apparent that there is now a portion of the thermoplastic flexible sheet 18 that has been drawn into the tubular member 21 to form a recessed surface 20.

FIG. 3 is also intended to convey what takes place when the heating unit 21 and vacuum pump 36 are idled and the entire apparatus is allowed to cool.

It should also be appreciated that the invention also contemplates that in another embodiment there be no differential pressure and the thermoplastic flexible barrier sheet 18, when softened, will simply be drawn by the force of gravity toward the tubular member. When this occurs, the softened thermoplastic flexible sheet 18 will take on a new shape, such that at least portion of the tubular member 21 becomes sandwiched between the softened flexible sheet and the plate 27, which acts as a support means.

Figure 4:
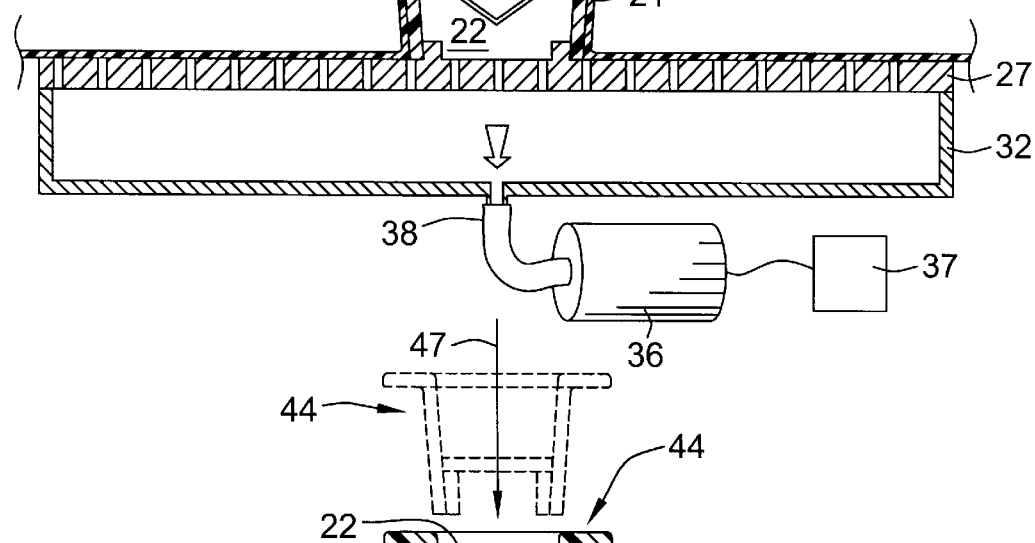
FIG. 4 illustrates a way to create an opening in a recessed region of a thermoplastic sheet.

Turning now to FIG. 4 there is shown a fully cooled and formed resuscitation mask. Centrally disposed in this figure and shown in broken outline above the tubular member 21 and its central opening 22 is a cutting blade 34 with arrow 35 indicating the direction of travel the blade 34 is to make to cut through the recessed surface, see FIG. 3, to create an opening through the thermoplastic flexible sheet 18. Immediately beneath the cutting blade 34 there is shown in full line the cutting blade 34 piercing the recessed surface 20.

Figure 5:
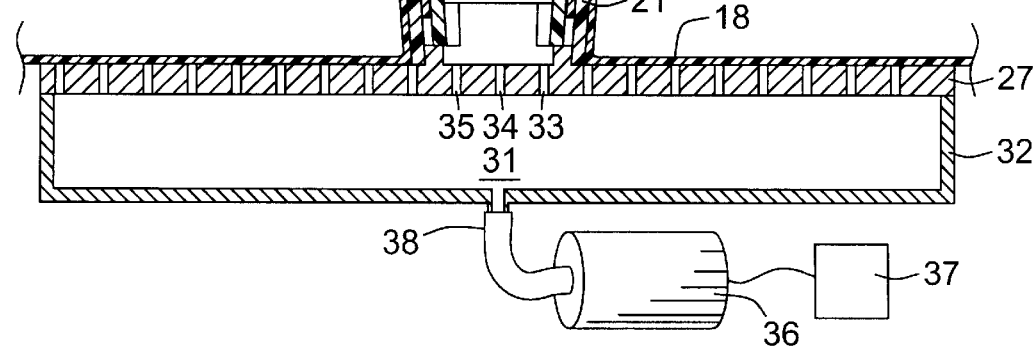
FIG. 5 depicts a manner of installing an insert in the form of a collar into an opening in the thermoplastic sheet of FIG. 4.

A glance at FIG. 5 reveals that positioned in a space at the top of this figure there is shown in broken a line a representation of an insect/collar 44. An overall sense of the entire shape of this insert/collar 44 may best be appreciated by reference to FIG. 5, where directly beneath the broken line representation of the inset/collar 44 just noted, there is shown in solid line the insert/collar 44 positioned in place in the central opening 22. It will be noted that a solid line arrow 47 is shown passing through the broken line representation of the insert/collar 44. The arrow 47 is intended to a convey a method step of inserting the insert/collar 44 into the tubular member 21 through the central opening 22 in the tubular member and an opening created in the recessed surface 20, FIG. 4 of thermoplastic flexible sheet 18. When the insert/collar 44 is pressed into place as shown in full line in this figure, there arises a seal between the tubular member 21, the flexible thermoplastic sheet 18, where this sheet 18 enters the central opening 22, and the insert/collar 44. When attention is focused on FIG. 5a of a partial section of an insert collar 44, it will be seen that there is included within the insert collar 44 a one-way valve 45 and a filter 46. The details of the one-way valve 45 and filter 46 do not form a part of the invention and are therefore not shown. Accordingly any suitable state-of-the-art one-way valve and/or filter may be employed in the final product that embodies the invention.

FIG. 6 displays the resuscitation mask 55 with portions of the flexible barrier sheet 18 removed. An arrow 60 is intended to convey the idea that when a force is applied to the tubular member 21 in the direction shown, the sleeve 19 and the mask 55 take on the general appearance shown in FIGS. 7 and 8.

FIG. 9 is an outline of a mannequin's head 61 having a circular mouth opening 62. In FIG. 10 a prior art type of mask 63 is shown schematically disposed over the mannequin's mouth 62. The circular mannequin mouth openings are of such a size that the tubular member 64 cannot fit within the circular opening 62. In situations where an individual is being trained in the use of this type of resuscitation mask, the poor fit of the mask with the mannequin significantly diminishes the reality of the simulated resuscitation attempt. FIG. 11 shows a resuscitation mask 55 embodying the invention, fitted snugly over the mannequin face. When a mask 55 embodying the invention is used in training, the training experience most nearly simulates reality, which will produce a higher level of trainee confidence when the training is finished. While FIG. 11 depicts a mannequin head it will also be appreciated that where a victim is an infant with a small mouth or an individual with teeth clenched shut, the resuscitation mask 55 embodying the invention also finds great utility without being converted to a more conventional configuration where the tubular member may be inserted into a victim's mouth. Inserting the tubular member into the victim's mouth, when possible, has the advantage of acting as a bite clock, which aids in keeping the mouth open.

Though the invention has been described with respect to a specific preferred embodiment thereof, many variations and modifications will immediately become apparent to those skilled in the art. It is therefore the intention that the appended claims be interpreted as broadly as possible in view of the prior art to include such variations and modifications.

What I claim as new:

1. A method of differential pressure forming a resuscitation mask of the type that may include a one-way valve and does include a thermoplastic flexible barrier sheet hermetically secured to a tubular member through which air is delivered from a rescuer's mouth to a victim's mouth and lungs, said method comprised of the following steps:

(a) placing said tubular member in engagement with a porous plate such that a central axis of said tubular member is essentially perpendicular to said porous plate, (b) locating said thermoplastic flexible barrier sheet between said tubular member and a source of heat, (c) activating said source of heat to soften said thermoplastic flexible barrier sheet;

(d) establishing a low pressure region on a side of said porous plate opposite to the porous plate side on which said tubular member has engaged said porous plate, said low pressure region thereby causing a differential pressure across said porous plate that results in said softened thermoplastic flexible barrier sheet being drawn towards said tubular member and taking on a new shape such that at least a portion of said tubular member becomes sandwiched between said softened flexible sheet and said porous plate, a portion of said softened thermoplastic flexible sheet being drawn across said tubular member;

(e) cooling said softened thermoplastic flexible barrier sheet to thereby cause said flexible thermoplastic sheet to maintain its new shape;

(f) creating an opening through said flexible sheet in a region where said surface is defined by the tubular member, and (g) inserting into said tubular member through said opening in said flexible thermoplastic sheet an insert means that mates with said flexible sheet to form a seal between said tubular member, said flexible thermoplastic sheet and said insert means.

2. The method claim 1 wherein said insert means includes integral therewith a one-way valve.

3. The method of claim 1 wherein said insert means includes a filter.

4. The method of claim 2 wherein said insert means further includes a filter.

5. A method of forming a resuscitation mask of the type that may include a one-way valve and does include a thermoplastic flexible barrier sheet hermetically secured to a tubular member through which air is delivered from a rescuer's mouth to a victim's mouth and lungs, said method comprised of the following steps:

(a) placing a tubular member in engagement with a support means such that a central axis of said tubular member is essentially perpendicular to said support means, (b) locating said thermoplastic flexible barrier sheet between said tubular member and a source of heat, (b) activating said source of heat to soften said thermoplastic flexible barrier sheet;

(c) drawing said softened thermoplastic flexible barrier sheet toward said tubular member placed on said support means to thereby cover said tubular member and take on a new shape such that at least a portion of said tubular member becomes sandwiched between said softened flexible sheet and said support means, and (d) cooling said softened thermoplastic flexible barrier sheet to thereby cause said flexible thermoplastic sheet to maintain its new shape; and (e) creating an opening through said flexible sheet in a region where said surface is defined by the tubular member.

6. The method of claim 5 wherein said method further includes the step of:

Inserting into said tubular member through said opening in said flexible thermoplastic sheet an insert means that mates with said flexible sheet to form a seal between said tubular member, said flexible thermoplastic sheet and said insert means.

7. The method of claim 5 where the drawing of said softened thermoplastic flexible barrier sheet toward said tubular member placed upon said support means is accomplished by having said support means take the form of a porous plate and causing a differential pressure across said porous plate that results in said softened thermoplastic flexible barrier sheet being drawn toward said tubular member.

8. The method of claim 5 where the drawing of said softened thermoplastic flexible barrier sheet toward said tubular member placed upon said support means is accomplished by gravity.

9. The method of claim 6 wherein said insert means includes integral therewith a one-way valve.

10. The method of claim 6 wherein said insert means further includes a filter.

11. The method of claim 9 wherein said insert means further includes a filter.

* * * * *